United States Patent [19]

Inukai et al.

[11] Patent Number: 5,803,911
[45] Date of Patent: Sep. 8, 1998

[54] ELECTROCARDIOGRAPHIC WAVEFORM DETECTION SYSTEM

[75] Inventors: Hidekatsu Inukai, Nagoya; Hiroshi Sakai, deceased, late of Komaki, both of Japan, by Hiroko Sakai, his legal heir

[73] Assignee: Colin Corporation, Komaki, Japan

[21] Appl. No.: 851,497

[22] Filed: May 5, 1997

[51] Int. Cl.⁶ .................................................. A61B 5/04
[52] U.S. Cl. .......................................... 600/387; 600/513
[58] Field of Search .................................. 600/382, 387, 600/391, 395, 513

[56] References Cited

U.S. PATENT DOCUMENTS 3,568,663  3/1971  Phipps .
4,248,243  2/1981  Niess et al. .
4,771,784  9/1988  Kozin et al. .

FOREIGN PATENT DOCUMENTS

0000759  2/1979  European Pat. Off. .
2709668  9/1978  Germany .
6-89504  4/1994  Japan .

Primary Examiner—William E. Kamm
Assistant Examiner—Carl H. Layno
Attorney, Agent, or Firm—Oliff & Berridge, PLC

[57] ABSTRACT

A system for reliably and accurately measuring the electrocardiographic waveform generated by a subject's cardiac muscle includes electrocardio electrodes that have multiple openings on their surfaces, a body contact determination circuit for determining if a subject is in physical contact with the electrocardio electrodes, a blow control circuit for causing air to flow out of the multiple openings of the electrocardio electrode when the subject is not in physical contact with the electrocardio electrodes and a suction control circuit for causing air to be sucked through the multiple openings of the electrocardio electrodes when the subject is in physical contact with the electrocardio electrodes. In a preferred embodiment, a pulse wave propagation velocity determining circuit is used to determine the propagation velocity of a subject's pulse wave.

33 Claims, 7 Drawing Sheets

ELECTROCARDIOGRAPHIC WAVEFORM DETECTION SYSTEM

BACKGROUND OF THE INVENTION

1. Field of Invention

This invention relates to systems for measuring the electrocardiographic waveform of a living subject. More specifically, this invention is directed to a system that reliably and accurately measures the electrocardiographic waveform of a living subject.

2. Description of Related Art

A device for measuring the electrocardiographic waveform of a living subject typically includes an arm cuff that measures the blood pressure of the living subject, a first arm rest that supports the arm of the subject that is placed through the arm cuff and a second arm rest that supports the other arm of the subject. The first and second arm rests each have an electrocardio electrode for measuring the electrocardiographic waveform of the subject. The electrodes are positioned so that they contact either the hand or the arm of the subject when the subject's arms are resting on the arm rests.

To obtain a reliable and stable electrocardiographic waveform, the contact resistance between the electrocardio electrodes and the skin of the subject must be low. Prior art devices have attempted to reduce the contact resistance between the electrode and the subject's skin by using a variety of techniques. Some prior art devices require that the subject consciously apply pressure to the electrode to reduce the contact resistance between the subject's skin and the electrode. This is not a reliable method because it relies on the cooperation of the subject being tested.

Other prior art devices utilize a suction cup for each electrocardio electrode. The resulting suction attracts the subject's skin to the electrode and helps decrease the contact resistance between the electrode and the subject's skin. However, dirt and dust collect on the electrode surface. The dirt and dust on the electrode surface increase the contact resistance between the electrode and the subject's skin. In addition, the stability and reliability of the electrocardiographic waveform measurement is partially dependent on the subject's cooperation. For example, if the subject moves too much during the measurement process, the accuracy of the resulting electrocardiographic waveform measurement goes down.

SUMMARY OF THE INVENTION

This invention provides a system for reliably and accurately measuring the electrocardiographic waveform generated by a subject's cardiac muscle. The system provides electrocardio electrodes that have multiple openings on their surfaces. A body contact determination circuit determines if a subject is in physical contact with the electrocardio electrodes. A blow control circuit causes air to flow out of the multiple openings in the electrocardio electrode when the subject is not in physical contact with the electrocardio electrodes. A suction control circuit causes air to be sucked through the multiple openings in the electrocardio electrodes when the contact determination circuit determines that the electrocardio electrodes are in physical contact with the subject.

The flow of air out of the multiple openings of the electrocardio electrode, when the electrocardio electrode is not in contact with the subject, reduces the accumulation of dust and dirt on the electrocardio electrode. In addition, the suction created when the electrocardio electrode comes into contact with the subject helps secure the subject's skin to the electrocardio electrode during the measurement process. In a preferred embodiment, pulse wave propagation velocity determining means are used to determine the propagation velocity of a subject's pulse wave.

These and other features and advantages of this invention are described in or are apparent from the following detailed description of the preferred embodiments.

BRIEF DESCRIPTION OF THE DRAWINGS

The preferred embodiments of this invention will be described in detail, with reference to the following figures, wherein.

DETAILED DESCRIPTION OF PREFERRED EMBODIMENTS

Figure 1:
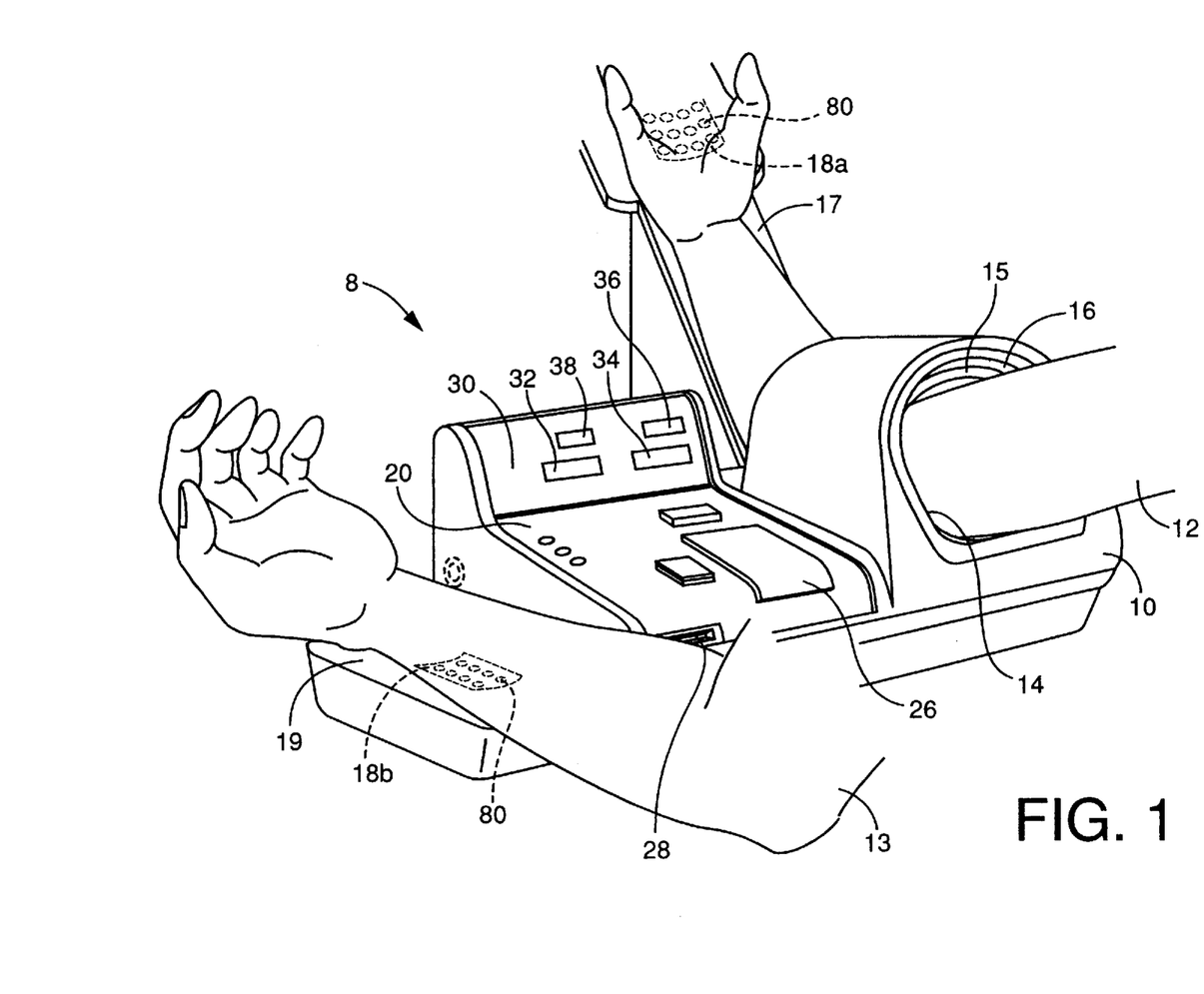
FIG. 1 is a perspective view of an automatic blood pressure measurement device incorporating the electrocardiographic waveform detection system of this invention.

FIG. 1 shows an automatic blood pressure measurement device 8 that incorporates the electrocardiographic waveform detection system of this invention. The device 8 comprises a housing 10 that includes an arm receptor 14 for receiving a right arm 12 of a subject for measuring the subject's blood pressure. A belt 16 is supported inside the arm receptor 14 in a generally cylindrical shape. An inflatable cuff 15, which is preferably formed by a rubber bag that is positioned inside a flexible cloth bag, is secured to the inner surface of the belt 16.

In the rear of the arm receptor 14, a first arm rest 17 is provided at a tilt to support the forearm of the subject's right arm 12. A first electrocardio electrode 18a is positioned on the arm rest 17 so that the electrocardio electrode 18a contacts the back of the hand of the subject's right arm 12 when the forearm is supported by the arm rest 17. The upper surface of the arm rest 17 has a shape suitable for supporting the subject's right forearm. Thus, the muscles between the elbow and the back of the hand are maintained in a relaxed state for a more accurate detection of the subject's electrocardiographic waveform.

A second arm rest 19 is provided on the left hand side of the housing 10 for supporting the subject's left arm 13. A second electrocardio electrode 18b is positioned on a middle portion of the arm rest 19. Thus, the second electrocardio electrode 18b contacts the subject's left arm 13 when the left arm 13 is supported by the second arm rest 19. The upper surface of the second arm rest 19 has a shape suitable for supporting the subject's entire left forearm. Thus, the muscles between the elbow and the back of the hand are maintained in a relaxed state for a more accurate detection of the subject's electrocardiographic waveform. The two electrocardio electrodes 18 cooperate with each other to detect the electrocardiographic waveform of the subject The automatic blood pressure measuring device 8 has an operation panel 20 that includes a printer 26 and a card insertion slot 28. The automatic blood pressure device 8 also has a display panel 30 that includes a systolic blood pressure display 32, a diastolic blood pressure display 34, a heart rate display 36 and a date and time display 38.

Figure 2:
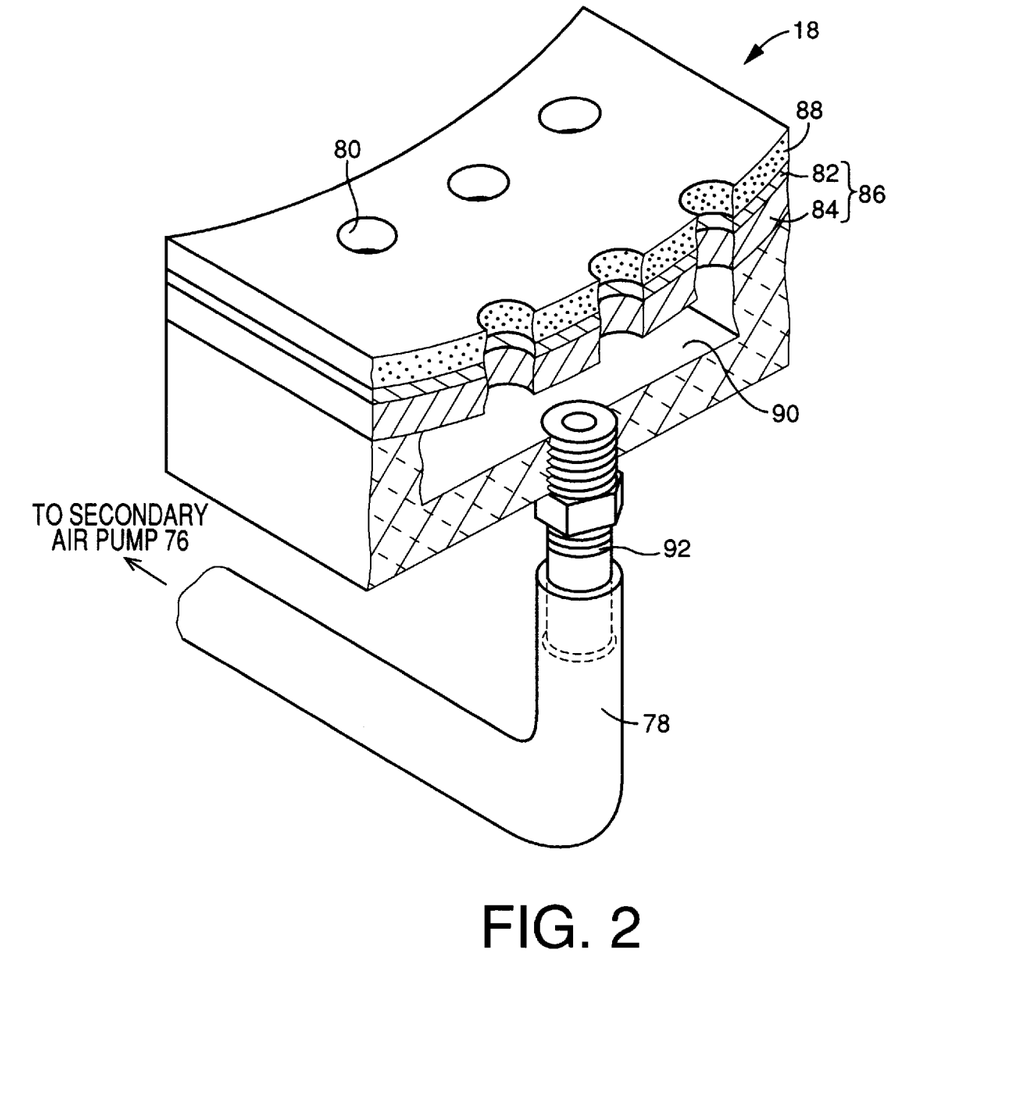
FIG. 2 is a sectional view of a preferred embodiment of an electrocardio electrode used in the automatic blood pressure measurement device of FIG. 1.

FIG. 2 shows a preferred embodiment of the electrocardio electrodes 18 used in the automatic blood pressure measurement device 8 of FIG. 1. A print board 86 is formed from a support layer 84 and an electrically conductive layer 82. The support layer 84 is preferably formed from epoxy resin. The electrically conductive layer 82 is preferably formed from copper foil. The electrically conductive layer 82 is preferably attached to the support layer 84 with an adhesive.

An electrically conductive adhesive material 88 is preferably attached to the electrically conductive layer 82, preferably with an adhesive. The electrically conductive adhesive material 88 is preferably a material known as "AMPS11" disclosed in Laid-Open Japanese Patent Application No. 6-29504. AMPS11 is an electrically conductive adhesive material with the following composition (by weight): (1) 20%–60% 2-acrylamide-2-methylpropanesulphonic acid and/or its salt; (2) 10%–40% polyhydric alcohol; (3) 10%–60% water; and (4) 0.1%–5% cross-linking agent.

The outer surface of the electrically conductive adhesive material 88, i.e., the surface that contacts the living subject, is preferably curved to increase the contact area between the electrically conductive adhesive material 88 and the right arm 12 of the living subject. In addition, a plurality of openings 80 extend through the electrically conductive adhesive material 88 and the print board 86.

The print board 86 is attached to a pressure chamber 90 that is preferably formed from aluminum. An air hose 78 is attached to the pressure chamber 90, preferably via an air nipple 92 that is screwed into the bottom of the pressure chamber 90.

Figure 3:
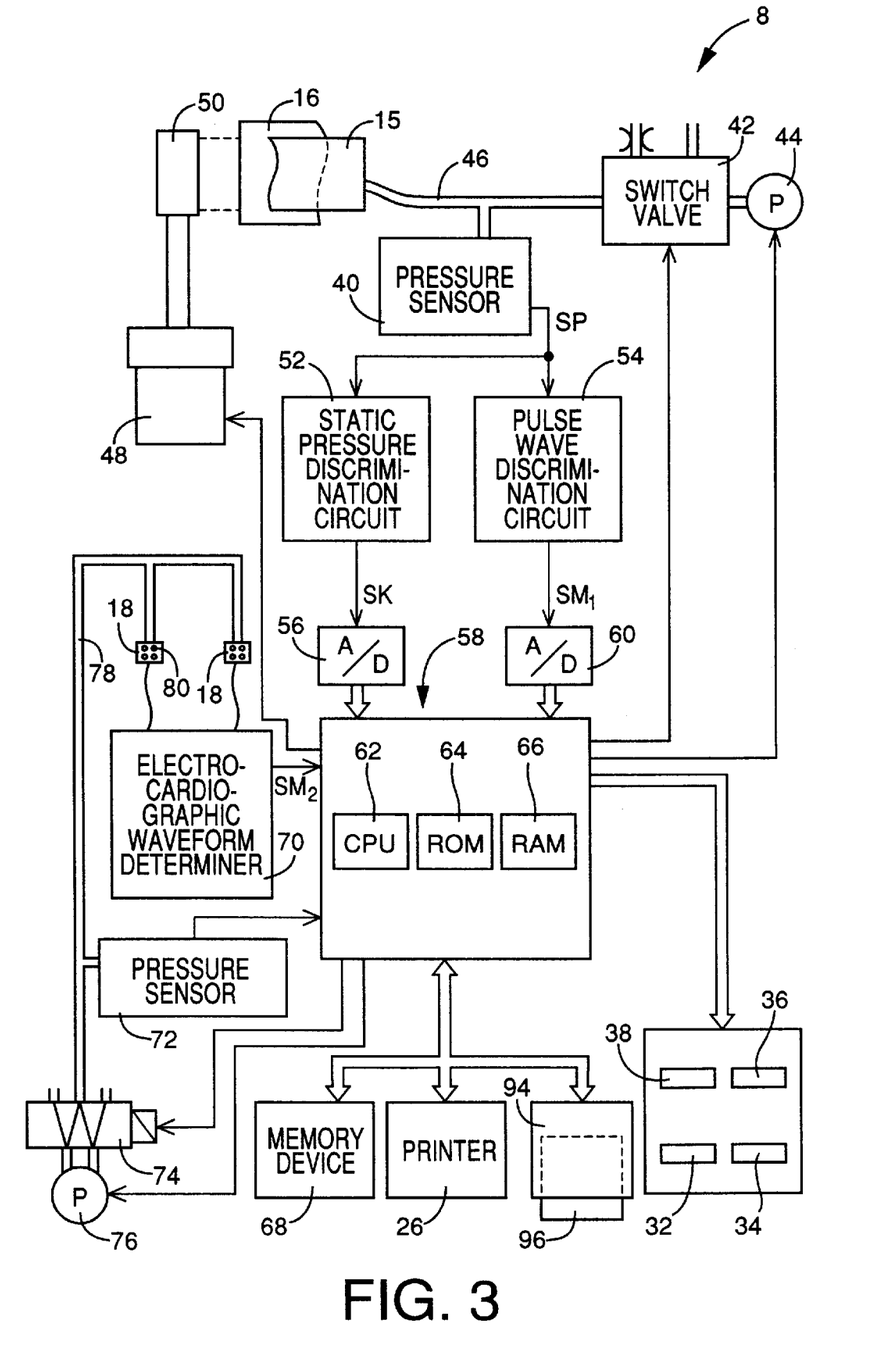
FIG. 3 is a block diagram of the automatic blood pressure measurement device of FIG. 1.

FIG. 3 shows a preferred embodiment of the electrocardiographic waveform detection system of this invention. The inflatable cuff 15 is connected via piping 46 to a pressure sensor 40, a switch valve 42 and a primary air pump 44.

The switch valve 42 is selectively placed in either an inflation position, a slow-deflation position or a quick-deflation position. In the inflation position, the switch valve 42 allows pressurized air from the primary air pump 44 to be supplied to the inflatable cuff 15. In the slow-deflation position, the switch valve 42 allows the pressurized air in the inflatable cuff 15 to be slowly discharged. In the quick-deflation position, the switch valve 42 allows the pressurized air in the inflatable cuff 15 to be quickly discharged.

The belt 16, which is supported in a cylindrical shape by the arm receptor 14 and to which the inflatable cuff 15 is secured, is attached at one of its longitudinal ends to the housing 10. The other longitudinal end of the belt 16 is attached to a rotatable drum 50 that is driven or rotated by a direct-current motor 48 via reduction gears. The belt 16/inflatable cuff 15 combination is tightened and loosened by the motor 48. The pressure sensor 40 detects an air pressure in the inflatable cuff 15 and supplies a pressure signal SP, representing the detected pressure, to a static pressure discrimination circuit 52 and a pulse wave discrimination circuit 54. The static pressure discrimination circuit 52 includes a low-pass filter that extracts a static component contained in the pressure signal SP, i.e., a cuff pressure signal SK that represents the static cuff pressure. The cuff pressure signal SK is supplied to an electronic control device 58 via a first A/D converter 56.

The pulse wave discrimination circuit 54 includes a band-pass filter that extracts an oscillatory component of the pressure signal SP that falls within a predetermined frequency range. The oscillatory component is supplied as cuff pulse wave signal $SM_1$ to the electronic control device 58 via a second A/D converter 60. The cuff pulse wave signal $SM_1$ represents an oscillatory pressure wave that is produced from a brachial artery of the subject and that propagates to an area on the subject's right arm 12 that is in contact with the inflatable cuff 15.

The inflatable cuff 15, the pressure sensor 40, the pulse wave discrimination circuit 54, the static pressure discrimination circuit 52 and the A/D converters 56 and 60 cooperate with one another to provide a pulse wave sensor that detects a pulse wave that propagates through an artery of the living subject.

The electronic control device 58 preferably includes a central processing unit (CPU) 62, a read-only memory (ROM) 64, a random-access memory (RAM) 66 and an input-output (I/O) port (not shown). The CPU 62 processes input signals according to control programs pre-stored in the ROM 64 by using the RAM 66 as temporary storage. In addition, the CPU 62 outputs a drive signal to a printer 26, and outputs display signals to the displays 32, 34, 36 and 38.

When a blood pressure measurement is initiated, the CPU 62 supplies a drive signal to the DC motor 48. The DC motor 48 winds the belt 16 to tighten the inflatable cuff 15 around the subject's right arm 12.

Next, the CPU 62 supplies a drive signal to the primary air pump 44 to inflate the inflatable cuff 15, compressing the upper portion of the subject's right arm 12. The CPU 62 then supplies a drive signal to the switch valve 42 to gradually reduce the air pressure in the inflatable cuff 15.

While the air pressure in the inflatable cuff 15 is being gradually reduced, the CPU 62 obtains the pulse wave signal $SM_1$ and the cuff pressure signal SK from the pressure sensor 40 via the pulse wave discrimination circuit 54 and the static pressure discrimination circuit 52, respectively. The CPU 62 then determines the subject's systolic blood pressure value SBP and the subject's diastolic blood pressure value DBP based on the obtained signals $SM_1$ and SK using a well-known oscillometric blood pressure measuring method. The CPU 62 also determines the subject's average blood pressure value. The CPU 62 then supplies display signals to the systolic blood pressure display 32 and the diastolic blood pressure display 34 to display the determined blood pressure values SBP and DBP, respectively.

In addition, the CPU 62 produces a set of blood pressure data that represents the determined blood pressure values SBP and DBP, and that represents a date and a time when the blood pressure values were obtained. The CPU 62 stores the set of blood pressure data in a blood pressure data storing area of a memory device 68. The memory device 68 preferably stores a plurality of sets of blood pressure data produced in a plurality of blood pressure measuring operations. The memory device 68 may be implemented by any known data storing device, such as a magnetic disk, a magnetic tape, static or dynamic RAM, a floppy disk and disk drive, a writable optical disk and disk drive, a hard drive, flash memory or the like.

The automatic blood pressure measuring device 8 includes an electrocardiographic waveform determiner 70.

The electrocardiographic waveform determiner 70 continuously detects an electrocardiographic waveform that indicates the change in electric potential of the subject's cardiac muscle. The electrocardiographic waveform determiner 70 determines the electrocardiographic waveform from signals supplied by the pair of electrocardio electrodes 18. The electrocardiographic waveform determiner 70 supplies the electrocardiographic waveform to the electronic control device 58 as an electrocardio signal $SM_2$.

The pair of electrocardio electrodes 18 are connected via piping 78 to a pressure sensor 72, a switch valve 74 and a secondary air pump 76. The switch valve 74 is selectively placed in either a blowing state or a suction state. In the blow state, the switch valve 74 allows air to flow out of the pair of electrocardio electrodes 18 through the openings 80. In the suction state, the switch valve 74 allows air to be sucked in through the openings 80 of the pair of electrocardio electrodes 18.

Figure 4:
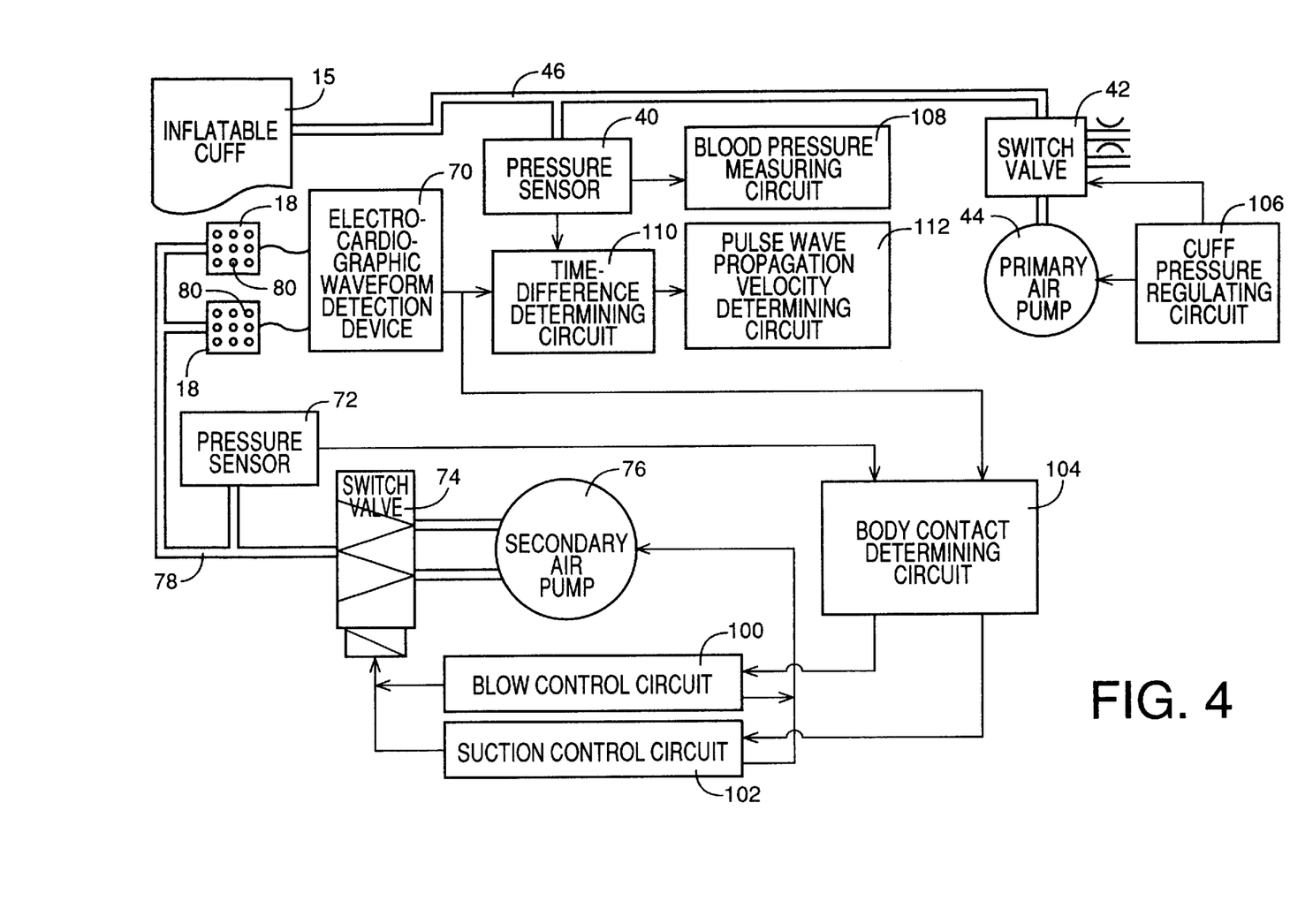
FIG. 4 is a block diagram of an electronic control device of the automatic blood pressure measurement device of FIG. 1.

FIG. 4 illustrates the control functions of the electronic control device 58 of the automatic blood pressure measuring device 8. The electronic control device 58 regulates whether air is blown out of or sucked through the openings 80 of the electrocardio electrodes 18.

To blow air out of the openings 80, a blow control circuit 100 switches the switch valve 74 to the blow state and drives the secondary air pump 76 to provide a flow of air to the openings 80. To suck air through the openings 80, a suction control circuit 102 switches the switch valve 74 to the suction state and drives the secondary air pump 76 to suck air through the openings 80.

A body contact determining circuit 104 determines whether the subject's arms are in physical contact with the electrocardio electrodes 18. When a blood pressure measurement is not being taken, the electronic control device 58 is preferably in the blow state, which means that air is blown through the openings 80 of the electrocardio electrodes 18. When the subject's arms are placed on the electrocardio electrodes 18, the subject's arms obstruct the openings 80. The obstruction of the openings 80 causes an increase in the air pressure in the piping 78, which is sensed by the pressure sensor 72. The body contact determining circuit 104 determines that both arms of the subject are in contact with the electrocardio electrodes 18 when the pressure sensed by the pressure sensor 40 exceeds a predetermined value. The body contact determining circuit 104 also determines that the arms of the subject are in contact with the electrocardio electrodes 18 when the electrocardiographic waveform determiner 70 receives electrocardiographic waveform signals from the electrocardio electrodes 18.

When the body contact determining circuit 104 determines that the arms of the subject are in contact with the electrocardio electrodes 18, it directs the blow control circuit 100 and the suction control circuit 102 to switch to the suction state, in which air is sucked through the openings 80 on the electrocardio electrodes 18. The suction created in the vicinity of the outer surface of the electrocardio electrodes 18 helps maintain the subject's arms in firm contact with the electrocardio electrodes 18.

The electronic control device 58 also regulates the air pressure in the inflatable cuff 15 via a cuff pressure regulating circuit 106. When a blood pressure measurement is initiated, the cuff pressure regulating circuit 106 switches the switch valve 42 to an inflation position and drives the primary air pump 44 to quickly increase the air pressure in the inflatable cuff 15 to a predetermined target value $P_1$, e.g., 180 mmHg. Subsequently, the cuff pressure regulating circuit 106 switches the switch valve 42 to a slow-deflation position to slowly decrease the air pressure in the inflatable cuff 15.

While the air pressure in the inflatable cuff 15 is slowly decreasing, blood pressure measuring circuit 108 uses a well-known oscillometric method to measure the subject's systolic blood pressure and the subject's diastolic blood pressure. The blood pressure measurement is based on the variation of the amplitudes of the heart beat-synchronous pulses of the cuff pulse wave (i.e., cuff pulse wave signal $SM_1$) obtained through the pulse wave discrimination circuit 54 while the air pressure in the inflatable cuff 15 is slowly decreased. The electronic control device 58 also measures the subject's heart rate based on the time gap between pulses of the cuff pulse wave.

Figure 5:
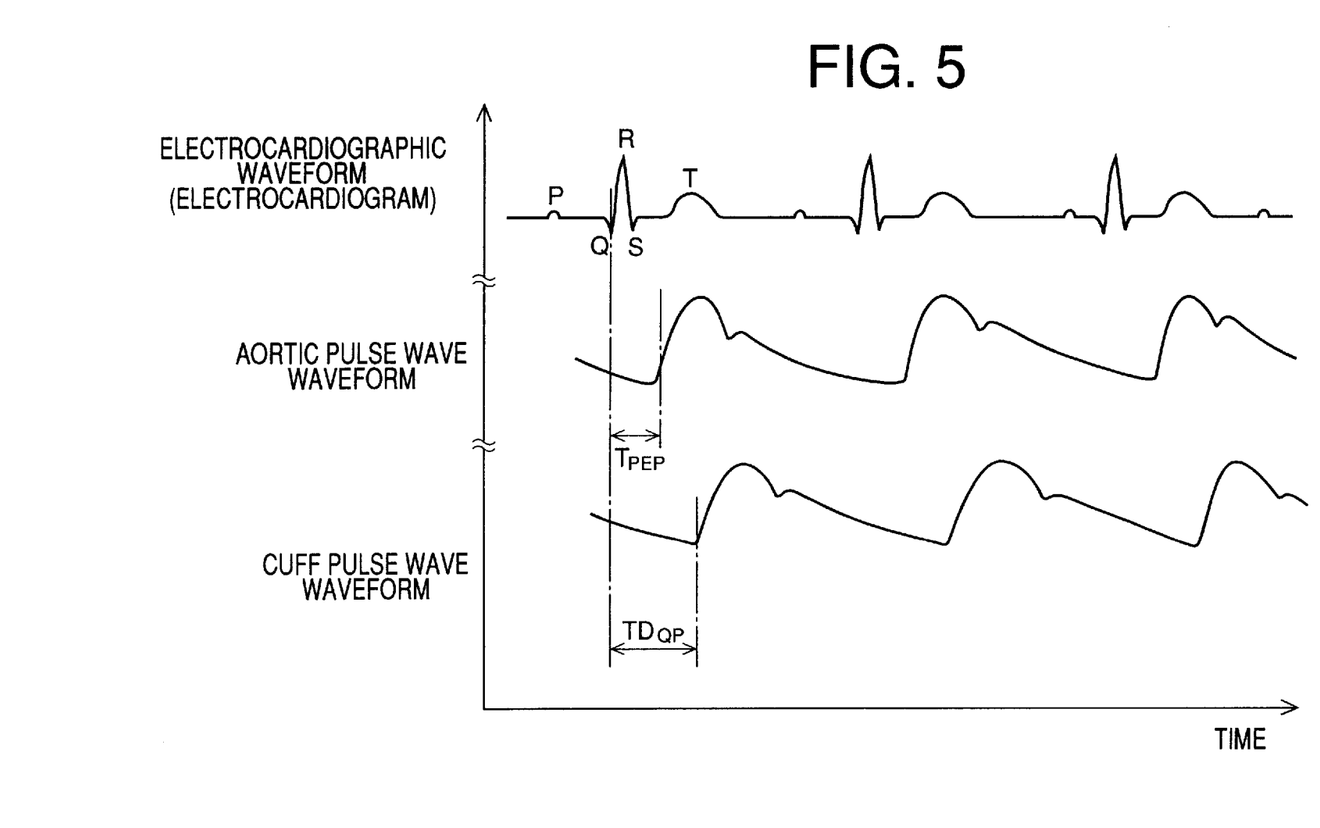
FIG. 5 is a timing chart of the electronic control device of the automatic blood pressure measurement device of FIG. 1.

In addition, a time-difference determining circuit 110 determines a time difference $TD_{QP}$ between a predetermined periodic point on the electrocardiographic waveform and a predetermined periodic point on the cuff pulse waveform when the air pressure in the inflatable cuff 15 is approximately equal to the subject's diastolic blood pressure. In the preferred embodiment, the time-difference determining circuit 110 determines the time-difference $TD_{QP}$ between a Q point on the electrocardiographic waveform and the rise point of the cuff pulse waveform, as shown in FIG. 5.

A pulse wave propagation velocity determining circuit 112 determines a propagation rate $V_M$ (m/sec) of the cuff pulse wave. The cuff pulse wave propagates through an artery of the subject, including the brachial artery of the subject's right arm 12. The pulse wave propagation velocity determining circuit 112 calculates the propagation velocity $V_M$ based on the calculated time difference $TD_{QP}$ according to the following formula:

$$V_M = L/(TD_{QP} - T_{PEP}) \tag{1}$$

where:

L is the length (m) of the subject's artery from the left ventricle to the point where the artery is pressing against the inflatable cuff 15 via the aorta and the brachial artery; and $T_{PEP}$ is the pre-ejection period between a Q wave of the electrocardiographic waveform and a minimum point (i.e., rising point) of the aortic pulse wave waveform. The values L and $T_{PEP}$ in Equation (1) are experimentally determined in advanced. Equation (1) is preferably prestored in the ROM 64.

Figure 6A:
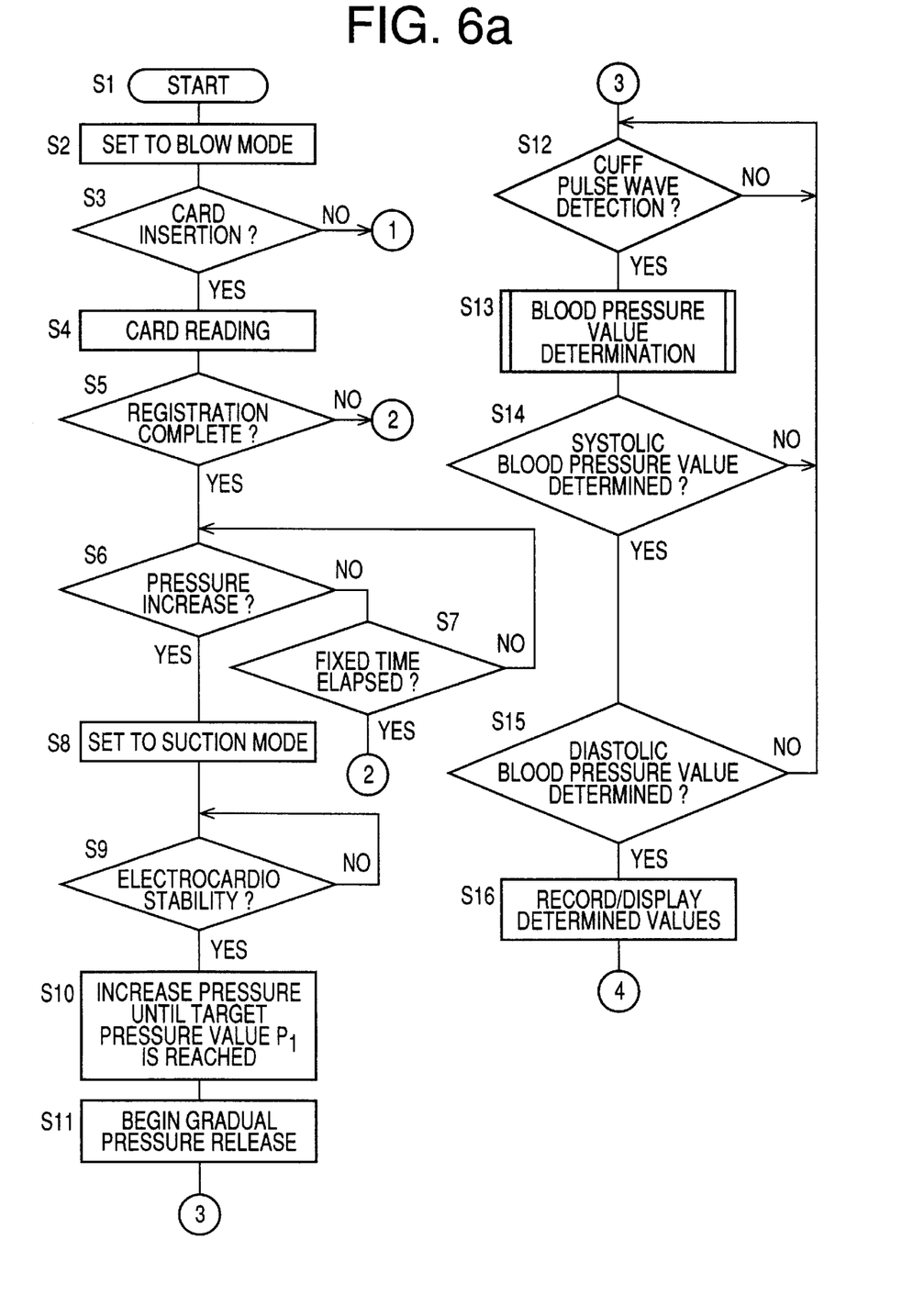
FIGS. 6a and 6b are flowcharts of a preferred control routine for the automatic blood pressure measurement device of FIG. 1.
Figure 6B:
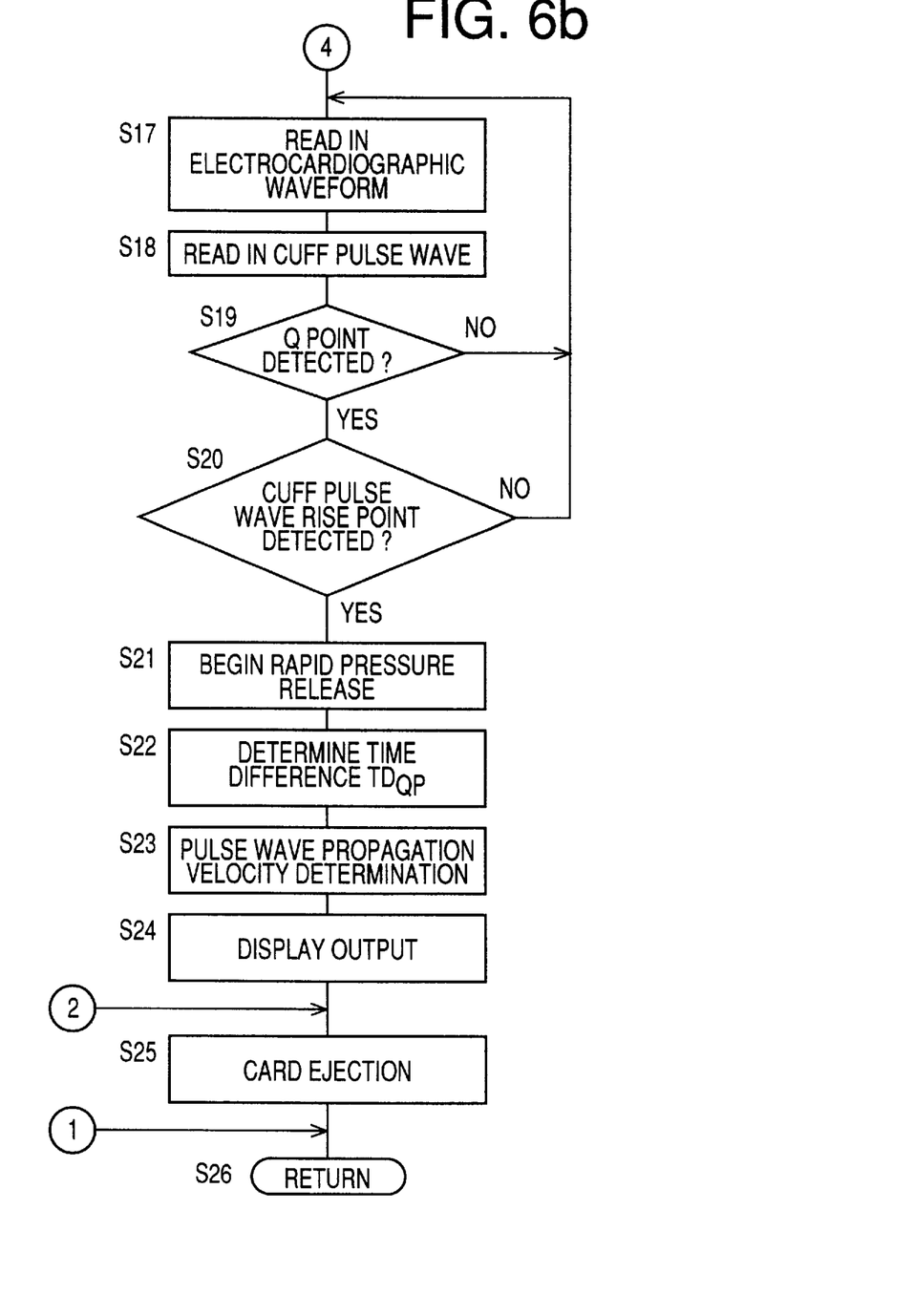

FIGS. 6a and 6b illustrate a preferred control routine for the electrocardiographic waveform detection system of this invention. The routine starts at step S1 and proceeds to step S2, where the control system starts the secondary air pump 76 and switches the switch valve 74 to the blow state to blow air through the openings 80 in the electrocardio electrodes 18. Control then continues to step S3, where the control system determines if a magnetic card 96 has been inserted into the card insertion opening 28 of the card reader 94. If a card has been inserted, control continues to step S4. Otherwise, control jumps to step S26, where the control routine returns to step S1.

In step S4, the control system reads an ID signal recorded on the magnetic card 96. Control then continues to step S5, where the control system determines if the ID signal corresponds to a pre-registered signal stored in the memory device 68. If the ID signal corresponds to the pre-registered signal, control continues to step S6. Otherwise, control jumps to step S25. In step S25, the magnetic card 96 is ejected from the card reader 94. Control then continues from step S25 to step S26.

In step S6, the control system determines if the pressure detected by the pressure sensor 72 exceeds a predetermined pressure value $P_A$. The predetermined pressure value $P_A$ is experimentally determined in advance, and corresponds to a pressure value that results from having the openings 80 on the electrocardio electrodes 18 covered by the subject's arms. If the detected pressure exceeds the predetermined pressure value $P_A$, control jumps to step S8. Otherwise, control continues to step S7.

In step S7, the control system determines if a predetermined period of time $T_A$ (e.g., 3 minutes) has elapsed. If the time period $T_A$ has elapsed, control jumps to step S25. Otherwise, control returns to step S6.

In step S8, the control system switches the switch valve 74 to the suction state to suck air from the openings 80 of the electrocardio electrodes 18. Control then continues to step S9, where the control system determines if the electrocardiographic waveform detected by the electrocardiographic waveform determiner 70 is stable. The control system determines if the electrocardiographic waveform is stable using a well-known method that determines whether a peak value of an R point on the electrocardiographic waveform is detected within a predetermined period of time. If the control system determines that the electrocardiographic waveform is stable, control continues to step S10. Otherwise, the control system returns to step S9.

In step S10, the control system increases the air pressure in the inflatable cuff 15 until the target pressure value $P_1$ is reached. The control system accomplishes this by driving the drum 50 to tighten the belt 16 and the inflatable cuff 15 around the subject's right arm 12. At the same time, the control system switches the switch valve 42 to the inflation position and turns on the primary air pump 44. When the air pressure in the inflatable cuff 15 reaches the predetermined pressure $P_1$, the control system stops the primary air pump 44. Control then continues to step S11.

In step S11, the control system switches the switch valve 42 to the slow-deflation position. Accordingly, the air pressure in the inflatable cuff 15 gradually decreases. Control then continues to step S12.

In step S12, the control system determines if the cuff pulse wave signal $SM_1$ has been detected. If the cuff pulse wave signal $SM_1$ is detected, control continues to step S13. Otherwise, control jumps back to step S12.

In step S13, the blood pressure measuring circuit determines the subject's systolic, diastolic and average blood pressure from the changes in the amplitudes in the cuff pulse waves detected during the slow release of air from the inflatable cuff 15. As discussed above, the subject's blood pressure is determined using a well-known oscillometric method. Control then continues to step S14, where the control system determines if the subject's systolic blood pressure has been determined. If the subject's systolic blood pressure has been determined, control continues to step S15. Otherwise, control returns to step S12 and steps S12–S14 are repeated.

In S15, the control system determines if the subject's diastolic blood pressure has been determined. If the subject's diastolic blood pressure has been determined, control continues to step S16. Otherwise, control returns to step S12 and steps S12–S15 are repeated.

In step S16, the control system stores the determined systolic blood pressure, the determined diastolic blood pressure, the determined average blood pressure, the determined heart rate, and the time and date of the measurement in the memory device 68. In addition, the control system displays the systolic blood pressure value on the display 32, the diastolic blood pressure value on the display 34 and the heart rate on the display 36.

Next, at step S17, the control system reads in the electrocardiographic waveform detected by the electrocardiographic waveform determiner 70. Control then continues to step S18, where the control system reads in the cuff pulse wave detected by the pressure sensor 40.

Next, in step S19, the control system determines whether the Q point on the electrocardiographic waveform has been detected. If the Q point on the electrocardiographic waveform is detected, control continues to step S20. Otherwise, control returns to step S17 and steps S17–S19 are repeated.

In step S20, the control system determines if the rise point of the cuff pulse wave has been detected. If the rise point of the cuff pulse wave is detected, control continues to step S21. Otherwise, control returns to step S17 and steps S17–S20 are repeated.

In step S21, the control system switches the switch valve 42 to the quick-deflation position to rapidly decrease the air pressure in the inflatable cuff 15. Control then continues to step S22, where the control system determines the time difference $TD_{QP}$ between the Q point of the electrocardiographic waveform and the rise point of the cuff pulse wave waveform.

Next, in step S23, the pulse wave propagation velocity determining circuit determines, using the Equation (1) discussed above, the cuff wave propagation velocity $V_M$ based on the time difference $TD_{QP}$ determined at step S22. Control then continues to step S24, where the control system prints out some or all of the measured values with the printer 26. Control then continues to step S25.

Because air is blown from the openings 80 of the electrocardio electrodes 18 when a measurement is not being taken, dust and dirt are kept from accumulating on the contact surface of the electrocardio electrodes 18. Accordingly, contact between the subject's skin and the electrocardio electrodes 18 is improved. This results in a more accurate and stable detection of the electrocardiographic waveform.

In addition, this electrocardiographic waveform detection system improves the contact between the subject's arms and the electrocardio electrodes 18 by causing air to be sucked from the openings 80 of the electrocardio electrodes 18 when the control system determines that the subject's arms are in contact with the electrocardio electrodes 18.

In the preferred embodiment, the electrocardiographic waveform detection system of this invention determines whether the subject's arms are in contact with the electrocardio electrodes 18 both by detecting, in step S6, the air pressure in the piping 78 and by determining, in step S9, if the electrocardiographic waveform is stable. This improves the accuracy of the contact determination.

In the conventional method, the cuff pulse wave propagation velocity is measured using a cuff pulse wave sensor that is applied to a carotid artery or a femoral artery of the subject with the help of trained medical personnel. In this conventional method, a skilled person is required to determine the best location on the skin to place the cuff pulse wave sensor. Therefore, it is considerably difficult for the subject to measure his or her own pulse propagation velocity. In contrast, the electrocardiographic waveform detection system of this invention can be easily operated by the subject without any special skill.

Furthermore, the electrocardiographic waveform detection system of this invention determines the pulse wave propagation velocity, the systolic blood pressure, the diastolic blood pressure and the average blood pressure concurrently. Accordingly, the subject is provided with more medical information.

In addition, in step S22, the time difference $TD_{QP}$ is determined based on the cuff pulse wave detected by the pressure sensor 40 when the air pressure in the inflatable cuff 15 is close to the subject's diastolic blood pressure. Generally, in a time period in which the cuff pressure is higher than the subject's average blood pressure, the time difference $TD_{QP}$ increases as the air pressure in the cuff decreases. However, when the air pressure in the cuff is approximately equal to the subject's diastolic blood pressure, the time difference $TD_{QP}$ is not influenced by changes in the air pressure in the inflatable cuff 15. Thus, the electrocardiographic waveform detection system of this invention determines a very accurate time difference $TD_{QP}$. Accordingly, the system also determines a very accurate cuff propagation velocity $V_M$.

The electronic control device 58, including the time-difference determining circuit 110, blow control circuit 100, suction control circuit 102, blood pressure measuring circuit 108, pulse wave propagation velocity determining circuit 112, body contact determining circuit 104 and cuff pressure regulating circuit 106, is preferably implemented on a programmed general purpose computer. However, the electronic control device 58 can also be implemented on a special purpose computer, a programmed microprocessor or microcontroller or peripheral integrated circuit elements, an ASIC or other integrated circuit, a hard wired electronic or logic circuit such as a discrete element circuit, or a programmable logic device such as a FPGA, a PLD, a PLA or a PAL, or the like. In general, any device on which a finite state machine capable of implementing the flowchart shown in FIG. 6 and controlling the peripheral devices shown in FIG. 3 can be used to implement the electronic control device 58 of this invention.

While this invention has been described in conjunction with the specific embodiment outlined above, it is evident that many alternatives, modifications and variations will be apparent to those skilled in the art. For example, although the arm receptor 14 in the automatic blood pressure measuring device 8 is adapted to receive the subject's right arm 12, it is possible to modify the automatic blood pressure measuring device 8 to receive the subject's left arm 13 through the arm receptor 14. In this configuration, the arm receptor 14 and the first arm rest 17 are provided on the left half portion of the housing 10, and the second arm rest 19 is provided on the right hand side of the housing 10.

In addition, although the first arm rest 17 is provided at a tilt, the arm rest 17 may also be formed to extend in a horizontal direction. Furthermore, the second arm rest 19 may be provided at a tilt. In either case, the arm rests 17 and 19 are required to support the subject's arms 12 and 13 so that the muscles of the arms 12 and 13 are kept in a relaxed state.

Although an electrocardio electrode 18a is provided on the free end portion of the first arm rest 17 and an electrocardio electrode 18b is provided on the middle portion of the second arm rest 19, it is possible to position the electrocardio electrodes 18 at different positions on the arm rests 17 and 19. The positions of the electrocardio electrodes 18 will depend upon the shapes and positions of the arm rests 17 and 19.

In addition, although two separate air pumps are used for the primary air pump 44 and the secondary air pump 76, a single air pump may be used to drive both the inflatable cuff 15 and to provide air to the electrocardio electrodes 18. In this configuration, the piping 78 is connected to an air exhaust side of the air pump, and the piping 46 is connected to an air intake side of the air pump. When the switch valve 42 is set to an air exhaust state, the air pump will provide air to the openings 80 on the electrocardio electrodes 18 without affecting the air pressure in the inflatable cuff 15. By reversing the rotation of the air pump, air is input from the openings 80 and the air pressure in the inflatable cuff 15 is increased. Furthermore, a filter can be attached to the exhaust side of the air pump to prevent dirt and dust from building up in the openings 80 on the electrocardio electrodes 18.

Furthermore, although the electrocardiographic waveform detection system of this invention determines whether the subject's arms are in contact with the electrocardio electrodes 18 at steps S6 and S9, only one of these steps may be used. In addition, the electrically conductive adhesive layer 88 can be omitted.

Although the electrocardiographic waveform detection system has been shown in conjunction with an automatic blood pressure measurement device 8, it may also be used in conjunction with other systems. Furthermore, although $TD_{QP}$ has been defined as the time difference between a Q point of the electrocardiographic waveform and a rise point of the cuff pulse wave waveform, it may also be defined from an R point of the electrocardiographic waveform or from an S point of the electrocardiographic waveform. Because the time difference between a Q point, an R point and an S point on the electrocardiographic waveform is extremely small, any one of these points may be used to determine $TD_{QP}$.

Accordingly, the preferred embodiment of the invention as set forth above is intended to be illustrative, not limiting. Various changes may be made without departing from the spirit and scope of the invention as defined in the following claims.

What is claimed is:

1. An electrocardiographic waveform detection system for measuring an electrocardiographic waveform of a living subject, comprising:

at least one electrocardio electrode having a plurality of air openings, the at least one electrocardio electrode capable of detecting an electrocardiographic signal from the living subject when the living subject is in physical contact with the electrocardio electrode;

an air pump connected to the at least one electrocardio electrode;

a blow control circuit that controls the air pump to blow air out of the air openings of the at least one electrocardio electrode when the electrocardio electrode is not in physical contact with the living subject; and an electrocardiographic waveform determiner that determines the subject's electrocardiographic waveform based on the electrocardiographic signals from the at least one electrocardio electrode.

2. The electrocardiographic waveform detection system of claim 1, further comprising a body contact determining circuit that determines if the at least one electrocardio electrode is in physical contact with the living subject and, when the at least one electrocardio electrode is in physical contact with the living subject, controls the blow control circuit to stop blowing air out of the air openings of the at least one electrocardio electrode.

3. The electrocardiographic waveform detection system of claim 2, wherein the body contact determining circuit determines that the at least one electrocardio electrode is in physical contact with the living subject when a stable electrocardiographic signal is detected by the at least one electrocardio electrode.

4. The electrocardiographic waveform detection system of claim 2, further comprising an air pressure sensor connected between the at least one electrocardio electrode and the air pump, the air pressure sensor sensing an air pressure between the air pump and the at least one electrocardio electrode.

5. The electrocardiographic waveform detection system of claim 4, wherein the body contact determining circuit determines that the at least one electrocardio electrode is in physical contact with the living subject when the air pressure sensed by the pressure sensor exceeds a predetermined value.

6. The electrocardiographic waveform detection system of claim 1, wherein the at least one electrocardio electrode comprises:

a pressure chamber;

a support layer attached to the pressure chamber;

an electrically conductive layer attached to the support layer; and an electrically conductive adhesive layer attached to the electrically conductive layer;

wherein the plurality of air openings extend through the support layer, the electrically conductive layer and the electrically conductive adhesive.

7. The electrocardiographic waveform detection system of claim 6, wherein a surface of the electrically conductive adhesive layer that contacts the living subject during an electrocardiographic waveform measurement is curved to substantially follow a curvature of a body portion of the living subject.

8. An electrocardiographic waveform detection system for measuring an electrocardiographic waveform of a living subject, comprising:

at least one electrocardio electrode having a plurality of air openings, the at least one electrocardio electrode capable of detecting an electrocardiographic signal from the living subject when the living subject is in physical contact with the electrocardio electrode;

an air pump connected to the at least one electrocardio electrode;

a suction control circuit that controls the air pump to suck air through the air openings of the at least one electrocardio electrode when the electrocardio electrode is in physical contact with the living subject; and an electrocardiographic waveform determiner that determines the subject's electrocardiographic waveform based on the electrocardiographic signals from the at least one electrocardio electrode.

9. The electrocardiographic waveform detection system of claim 8, further comprising a body contact determining circuit that determines if the at least one electrocardio electrode is in physical contact with the living subject.

10. The electrocardiographic waveform detection system of claim 9, wherein the body contact determining circuit determines that the at least one electrocardio electrode is in physical contact with the living subject when a stable electrocardiographic signal is detected by the at least one electrocardio electrode.

11. The electrocardiographic waveform detection system of claim 9, further comprising an air pressure sensor connected between the at least one electrocardio electrode and the air pump, the air pressure sensor sensing an air pressure between the air pump and the at least one electrocardio electrode.

12. The electrocardiographic waveform detection system of claim 11, wherein the body contact determining circuit determines that the at least one electrocardio electrode is in physical contact with the living subject when the air pressure sensed by the pressure sensor exceeds a predetermined value.

13. The electrocardiographic waveform detection system of claim 8, wherein the at least one electrocardio electrode comprises:

a pressure chamber;

a support layer attached to the pressure chamber;

an electrically conductive layer attached to the support layer; and an electrically conductive adhesive layer attached to the electrically conductive layer;

wherein the plurality of air openings extend through the support layer, the electrically conductive layer and the electrically conductive adhesive.

14. The electrocardiographic waveform detection system of claim 13, wherein a surface of the electrically conductive adhesive layer that contacts the living subject during an electrocardiographic waveform measurement is curved to substantially follow a curvature of a body portion of the living subject.

15. An electrocardiographic waveform detection system for measuring an electrocardiographic waveform of a living subject, comprising:

at least one electrocardio electrode having a plurality of air openings, the at least one electrocardio electrode capable of detecting an electrocardiographic signal from the living subject when the living subject is in physical contact with the electrocardio electrode;

an air pump connected to the at least one electrocardio electrode;

a blow control circuit that controls the air pump to blow air out of the air openings of the at least one electrocardio electrode when the electrocardio electrode is not in physical contact with the living subject;

a suction control circuit that controls the air pump to suck air through the air openings of the at least one electrocardio electrode while the electrocardio electrode is in physical contact with the living subject; and an electrocardiographic waveform determiner that determines the subject's electrocardiographic waveform based on the electrocardiographic signals from the at least one electrocardio electrode.

16. The electrocardiographic waveform detection system of claim 15, further comprising a body contact determining circuit that determines if the at least one electrocardio electrode is in physical contact with the living subject.

17. The electrocardiographic waveform detection system of claim 16, wherein the body contact determining circuit determines that the at least one electrocardio electrode is in physical contact with the living subject when a stable electrocardiographic signal is detected by the at least one electrocardio electrode.

18. The electrocardiographic waveform detection system of claim 16, further comprising an air pressure sensor connected between the at least one electrocardio electrode and the air pump, the air pressure sensor sensing an air pressure between the air pump and the at least one electrocardio electrode.

19. The electrocardiographic waveform detection system of claim 18, wherein the body contact determining circuit determines that the at least one electrocardio electrode is in physical contact with the living subject when the air pressure sensed by the pressure sensor exceeds a predetermined value.

20. The electrocardiographic waveform detection system of claim 15, wherein the at least one electrocardio electrode comprises:

a pressure chamber;

a support layer attached to the pressure chamber;

an electrically conductive layer attached to the support layer; and an electrically conductive adhesive layer attached to the electrically conductive layer;

wherein the plurality of air openings extend through the support layer, the electrically conductive layer and the electrically conductive adhesive.

21. The electrocardiographic waveform detection system of claim 20, wherein a surface of the electrically conductive adhesive layer that contacts the living subject during an electrocardiographic waveform measurement is curved to substantially follow a curvature of a body portion of the living subject.

22. The electrocardiographic waveform detection system of claim 15, further comprising a time-difference determining circuit that determines a time difference between a predetermined periodic point on an electrocardiographic waveform of the living subject and a predetermined periodic point on a pulse waveform of the living subject.

23. An automatic blood pressure measurement device for measuring a blood pressure and an electrocardiographic waveform of a living subject, comprising:

a frame;

a first arm rest attached to the frame and capable of supporting a right arm of the living subject;

a first electrocardio electrode attached to the first arm rest and positioned to physically contact an arm of the living subject when the living subject's arm is resting on the first arm rest, the first electrode having a plurality of air openings and being capable of detecting an electrocardiographic signal from the living subject when the living subject is in physical contact with the first electrocardio electrode;

a second arm rest attached to the frame and capable of supporting a left arm of the living subject;

a second electrocardio electrode attached to the second arm rest and positioned to physically contact an arm of the living subject when the living subject's arm is resting on the second arm rest, the second electrode having a plurality of air openings and being capable of detecting an electrocardiographic signal from the living subject when the living subject is in physical contact with the second electrocardio electrode;

an air pump connected to the first and second electrocardio electrodes;

a blow control circuit that controls the air pump to blow air out of the air openings of the first and second electrocardio electrodes when the electrocardio electrodes are not in physical contact with the living subject;

a suction control circuit that controls the air pump to suck air through the air openings of the first and second electrocardio electrodes when the electrocardio electrodes are in physical contact with the living subject;

a blood pressure measuring circuit that measures a blood pressure of the living subject; and an electrocardiographic waveform determiner that determines the subject's electrocardiographic waveform based on the electrocardiographic signals from the first and second electrocardio electrodes.

24. The automatic blood pressure measurement device of claim 23, wherein the blood pressure measuring circuit measures a systolic blood pressure, a diastolic blood pressure and an average blood pressure.

25. The automatic blood pressure measurement device of claim 23, wherein the blood pressure measuring circuit comprises:

an arm receptor positioned on the frame to receive an arm of the living subject;

an inflatable cuff positioned inside the arm receptor capable of compressing an arm of the subject and detecting a cuff pulse waveform of the living subject; and an air pump connected to the inflatable cuff.

26. The automatic blood pressure measurement device of claim 23, further comprising a time-difference determining circuit that determines a time difference between a predetermined periodic point on an electrocardiographic waveform of the living subject and a predetermined periodic point on a cuff pulse waveform of the living subject.

27. The automatic blood pressure measurement device of claim 26, further comprising a pulse wave propagation velocity determining circuit that determines a propagation rate of a cuff pulse wave of the living subject based on the time difference determined by the time difference determining circuit.

28. The electrocardiographic waveform detection system of claim 23, further comprising a body contact determining circuit that determines if the first and second electrocardio electrodes are in physical contact with the living subject.

29. The electrocardiographic waveform detection system of claim 28, wherein the body contact determining circuit determines that the first and second electrocardio electrodes are in physical contact with the living subject when a stable electrocardiographic signal is detected by the first and second electrocardio electrodes.

30. The electrocardiographic waveform detection system of claim 28, further comprising an air pressure sensor connected between the first and second electrocardio electrodes and the air pump, the air pressure sensor sensing an air pressure between the air pump and the first and second electrocardio electrodes.

31. The electrocardiographic waveform detection system of claim 30, wherein the body contact determining circuit determines that the first and second electrocardio electrodes are in physical contact with the living subject when the air pressure sensed by the pressure sensor exceeds a predetermined value.

32. The electrocardiographic waveform detection system of claim 23, wherein each of the first and second electrocardio electrodes comprise:

a pressure chamber;

a support layer attached to the pressure chamber;

an electrically conductive layer attached to the support layer; and an electrically conductive adhesive layer attached to the electrically conductive layer;

wherein the plurality of air openings extend through the support layer, the electrically conductive layer and the electrically conductive adhesive.

33. The electrocardiographic waveform detection system of claim 32, wherein a surface of the electrically conductive adhesive layer that contacts the living subject during an electrocardiographic waveform measurement is curved to substantially follow a curvature of a body portion of the living subject.

* * * * *